United States Patent [19]

Kramer et al.

[11] Patent Number: 5,713,994
[45] Date of Patent: Feb. 3, 1998

US005713994A

[54] LOW-FUSING TEMPERATURE PORCELAIN, COMPOSITIONS, PROSTHESES, METHODS AND KITS

[75] Inventors: Carolyn M. Kramer, Moorestown; John F. McLaughlin, Lakehurst; Robert D. DeLuca, Pennington; John A. Hornor, Siklerville; Mary J. Daub, Mt. Laurel; Kevin A. Andino, Freehold, all of N.J.

[73] Assignee: Ceramco Inc., Burlington, N.J.

[21] Appl. No.: 660,996

[22] Filed: Jun. 10, 1996

[51] Int. Cl.$^6$ .............................. C03C 3/091
[52] U.S. Cl. .................. 106/35; 501/64; 501/66; 501/67; 501/70; 501/72; 433/223; 433/272.1; 433/167; 433/212.1; 433/208
[58] Field of Search .................. 106/35; 501/64, 501/66, 67, 70, 72; 433/223, 222.1, 167, 212.1, 208

[56] References Cited

U.S. PATENT DOCUMENTS

| | | | |
|---|---|---|---|
| 2,301,174 | 11/1942 | Dietz | 250/71 |
| 3,449,832 | 6/1969 | Connan | 32/8 |
| 4,167,417 | 9/1979 | Franz et al. | 106/35 |
| 4,481,036 | 11/1984 | Panzera | 106/35 |
| 4,645,454 | 2/1987 | Amdur et al. | 106/35 |
| 4,645,455 | 2/1987 | Kosmos | 433/203.1 |
| 4,806,383 | 2/1989 | Poltz | 106/35 |
| 4,839,313 | 6/1989 | Kondo et al. | 501/14 |
| 5,173,114 | 12/1992 | Heurtaux | 106/35 |
| 5,281,563 | 1/1994 | Komma et al. | 106/35 |
| 5,346,866 | 9/1994 | Komma et al. | 106/35 |
| 5,552,350 | 9/1996 | Hornor | 106/35 |

FOREIGN PATENT DOCUMENTS 2070691 12/1992 Canada.

OTHER PUBLICATIONS

John W. McLean; Dental Ceramics, Proceedings of the First International Symposium on Ceramics; 1983; pp. 516 and 517.

*Primary Examiner*—Melissa Bonner
*Attorney, Agent, or Firm*—Dale R. Lovercheck; James B. Bieber

[57] ABSTRACT

A low-fusing temperature porcelain compositions, methods of use thereof on metal or porcelain substrates to form dental prostheses and kits therefor. Compositions of the invention have a fusing temperature of less than 800° C. and a coefficient of thermal expansion compatible with a substrate of metal or ceramic. Each composition includes, in weight percent of the composition, from 40 to 65 percent by weight $SiO_2$, from 6 to 12 percent by weight $Al_2O_3$, from 6 to 12 percent by weight $Na_2O$, from 5.5 to 10.50 percent by weight $K_2O$, from 1 to 3 percent by weight $Li_2O$, from 0.8 to 2.5 percent by weight CaO, from 0.8 to 4.0 percent by weight $B_2O_3$ and from 0.1 to 0.8 percent by weight $CeO_2$.

26 Claims, No Drawings

LOW-FUSING TEMPERATURE PORCELAIN, COMPOSITIONS, PROSTHESES, METHODS AND KITS

This is a continuation-in-part of U.S. provisional patent application Ser. No. 60/012,125 filed Feb. 23, 1996.

FIELD OF THE INVENTION

The invention relates to porcelain compositions, dental prostheses, methods of use and kits thereof. More particularly the invention provides low-fusing temperature porcelain compositions, methods of use thereof on metal or porcelain substrates to form dental prostheses and kits therefor. The invention provides low-fusing porcelain paste opaque, low-fusing porcelain powder opaque, low-fusing porcelain crystals, low-fusing porcelain dentin and low-fusing porcelain transparent and opal enamels and low-fusing modifier porcelains including stains. The invention provides low-fusing porcelain having fluorescence, opalescence and which hold their shape when heated to temperatures between 750° C. and 800° C. Low-fusing porcelain in accordance with a preferred embodiment of the invention is polishable to high luster, and the smoothness of the polished porcelain results in at least about 50 percent to 90 percent less wear on natural tooth enamel than polished coventional porcelain. Preferably an angle from a line tangent to a point on a surface contour of a coating of porcelain composition of the invention has less than a 20 percent change during heating from 23° C. to 800° C. Preferably a physical surface feature of a dental prosthesis formed from a low-fusing temperature porcelain composition of the invention having a diameter (or longest dimension) of 0.5 mm retains a diameter (or longest dimension) of at least 0.25 mm after firing the prosthesis by heating from 23° C. to 800° C. and cooling from 800° C. to 23° C. five times.

BACKGROUND OF THE INVENTION

A dental prosthesis often comprises a crown or bridge restoration in which a dental porcelain is fused to a supporting metal or ceramic substrate. Dental porcelains are generally a mixture of glass, ceramic opacifiers, pigments and the like. There are a number of key considerations in selecting glass frit components to form a porcelain that will be compatible with the selected substrate. For example, the porcelain must have a coefficient of thermal expansion close to but less than that of the substrate. Otherwise, a porcelain fused to the substrate will tend to crack and separate from its supporting structure.

It is an object of the invention to provide a porcelain composition that has a low-fusing or processing temperature and a coefficient of thermal expansion such that it can be used in combination with both metal and porcelain substrates in dental prostheses, useful in making, repairing or improving crowns and bridges for both conventional restorations to natural dentition and to implant-based restorations.

Exemplary prior porcelain compositions are disclosed by Panzera in U.S. Pat. No. 4,481,036; Kosmos in U.S. Pat. No. 4,645,455; Kondo et al in U.S. Pat. No. 4,839,313; Heurtaux in U.S. Pat. No. 5,173,114; Komma et al in U.S. Pat. No. 5,281,563; Komma et al in U.S. Pat. No. 5,346,866.

SUMMARY OF THE INVENTION

A low-fusing temperature porcelain system for use in a dental prosthesis is provided. The porcelain system of the invention has components with compositions which include from 40 to 65 percent by weight $SiO_2$, from 6 to 12 percent by weight $Al_2O_3$, from 6 to 12 percent by weight $Na_2O$, from 5.5 to 12.5 percent by weight $K_2O$ (more preferably from 5.5 to 10.5 percent by weight $K_2O$), from 1 to 3 percent by weight $Li_2O$, from 0.8 to 2.5 percent by weight CaO, from 0.5 to 4 percent by weight $B_2O_3$ and from 0.1 to 0.8 percent by weight $CeO_2$. Preferably compositions of the invention include from 0.01 to 3.0 percent by weight $P_2O_5$.

A preferred embodiment of the invention provides a composition which includes from 58 to 65 percent by weight $SiO_2$, from 6 to 12 percent by weight $Al_2O_3$, from 7 to 12 percent by weight $Na_2O$, from 5.5 to 18.0 percent by weight $K_2O$, from 1.5 to 3 percent by weight $Li_2O$, from 1.2 to 2.5 percent by weight CaO and from 0.1 to 2.0 percent by weight $CeO_2$. Preferably the composition also includes from 0.01 to 3.0 percent by weight of $P_2O_5$.

A preferred embodiment of the invention provides a composition which includes from 40 to 47 percent by weight $SiO_2$, from 5 to 8 percent by weight $Al_2O_3$, from 6 to 12 percent by weight $Na_2O$, from 9.0 to 10.5 percent by weight $K_2O$, from 1 to 3 percent by weight $Li_2O$, from 0.8 to 3.0 percent by weight CaO, from 0.8 to 2.0 percent by weight $B_2O_3$ and from 0.3 to 1.0 percent by weight $CeO_2$.

The porcelain of the invention has a fusing temperature of less than 800° C. and a coefficient of thermal expansion compatible with a substrate of metal or ceramic. Preferably, the coefficient of thermal expansion is from about 11.5 to 13.4 ppm $°K^{-1}$ [from 30° to 430° C.], and more preferably 12.4 to 13.4 ppm $°K^{-1}$ [from 30° to 500° C.]

DETAILED DESCRIPTION OF THE INVENTION

The invention provides low-fusing temperature porcelain compositions, methods of use thereof on metal or porcelain substrates to form dental prostheses and kits therefor. The invention provides a low-fusing temperature porcelain system that is a mixture of oxides such that the resulting porcelain components have a fusing temperature of about 800° C. or less and a coefficient of thermal expansion of 11.5 to 12.5 ppm $°K^{-1}$ [30° to 430° C.]. The low-fusing porcelain may be employed in dental crowns, bridges, restorations and fixed dentures wherein it is fused to a substrate or coping of dental alloy copings, such as UltraCrown PD alloy distributed by Dentsply International (Ceramco), or fused to an appropriate all-ceramic substrate.

The compositional range for the low-fusing temperature dental porcelains of the invention, having processing temperatures of less than about 800° C. and a coefficient of thermal expansion (CTE) of 11.6 to 12.6 ppm $°K^{-1}$ [30° to 430° C.] is a mixture of oxides having from 40 to 65 percent by weight $SiO_2$, from 6 to 12 percent by weight $Al_2O_3$, from 6 to 12 percent by weight $Na_2O$, from 5.5 to 10.5 percent by weight $K_2O$, from 1 to 3 percent by weight $Li_2O$, from 0.8 to 2.5 percent by weight CaO, from 0.5 to 4 percent by weight $B_2O_3$ and from 0.1 to 0.8 percent by weight $CeO_2$.

Liquids containing 98 to 100 percent by weight water are preferably mixed with porcelain compositions of the invention in from a one to one weight ratio to a one (part liquid) to four (parts porcelain) weight ratio and more preferably in a weight ratio of from one (part liquid) to three (parts porcelain). For example, liquids contain 0.1 percent by weight of salts and/or preferably less than 0.5 percent by weight of organic liquids and/or less than 0.5 percent by weight solids dissolved in water are preferably mixed with porcelain compositions of the invention in a one (part liquid)

to three (parts porcelain) weight ratio. Carving liquids for use with porcelain are preferred for use with compositions of the invention for their ability to improve the handling and carving of porcelain and to reduce slumping during build-up and complete burn off at low temperatures. Also, Finesse Opaque Modifier Liquid and Finesse Stain Liquid are preferred for use in mixtures with porcelain compositions of the invention.

The low-fusing porcelain compositions of the invention are preferred for use in conjunction with non-precious or noble or high noble alloys when used for porcelain-fused-to-metal crowns, bridges or dental prostheses. The low-fusing porcelain components of the system preferably contain mixtures of frits, opacifiers and pigments in varied quantities to create an assortment of materials with a variety of fusion temperatures, translucencies and colors.

The low-fusing porcelain system of the invention is useful for fabricating porcelain-fused-to-metal restorations. All of the components fuse at temperatures approximately 200° C. lower than corresponding components of conventional dental porcelains such as Ceramco II and Ceramco II Silver porcelains. Preferably, each porcelain in the system has fluorescence. The use of these porcelains allows the dental technician to create a more aesthetic restoration at a lower temperature.

The low-fusing dentin and enamel porcelain compositions of the invention are also easier to polish and yield smoother and less abrasive surfaces than conventional porcelains. They contain fewer leucite crystals than conventional porcelains. The porcelain composition of the invention possess superior handling characteristics, making the creation of a restoration easier for the dental technician.

The compositions of the invention provide a lower fusing temperature than standard porcelain system. The compositions of the invention provide low-fusing opaque porcelains having a fusing temperature of 775° C.–790° C., compared to 975° C. for a standard dental porcelain. The compositions of the invention provide low-fusing dentin porcelains having a fusing temperature of from 700° C. to 760° C. more preferably from 720° C. to 740° C., compared to 920° C.–940° C. for a standard dentin porcelain.

The compositions of the invention provide thermal expansion compatible with a wider range of alloy compositions than Ceramco® II porcelain. The compositions of the invention provide low-fusing porcelains having a thermal expansion coefficient of 12.1 ppm/° C. at 430° C., compared to 12.5 ppm/° C. at 500° C. for Ceramco® II porcelain.

Compositions of the invention cause less wear against the opposing natural teeth (dentition) than standard porcelain systems. Low-fusing dentin porcelain of a preferred embodiment of the invention provides wear of $5.6 \times 10^{-2}$ mm$^2$ compared to $18.2 \times 10^{-2}$ mm$^2$ for Ceramco porcelain in a three body wear test. Low-fusing dentin porcelain of a preferred embodiment of the invention has a Vickers hardness of 520 kg/mm$^2$, compared to 620 kg/mm$^2$ for Ceramco II porcelain. The compositions of the invention when utilized in forming dental prostheses are characterized by having an easier polishability due to the reduced hardness compared to conventional porcelain compositions.

Examples 1–5 describe preparation and use of preferred compositions of the inventions shown in Table 1 and characteristics of the resulting dental porcelain qualities are shown in Table 2.

Example 1

A low-fusing temperature porcelain having the composition indicated in Table 1, under Example 1, is made by combining and fusing oxides, then pulverizing and blending with opacifiers and pigments. The resulting porcelain has a fusing temperature of less than 800° C. and a CTE of about 12.1 ppm ° K$^{-1}$ from 30° C. to 430° C. Samples of the resulting material have the characteristics and properties shown in Table 2 for low-fusing powder opaque when fired according to the schedule of Table 3. The schedule for firing includes 3 minutes of drying, 3 minutes of preheating at 450° C. and heating from 450° C. to 785° C. under a vacuum of 29 inches of Hg at a rate of 90° C. per minute, at 765° C. the vacuum is released and heating is continued to 785° C.

Example 1A

Low-fusing porcelain compositions of Example 1A of the invention are made in the same manner as Example 1, except having the compositions indicated in Table 1, under Example 1A.

Example 2

Low-fusing porcelain compositions of Example 2 of the invention are made in the same manner as Example 1, except having the compositions indicated in Table 1, under Example 2.

Example 2A

The procedure of Example 1 is followed except that the composition indicated in Table 1A launder Example 2A is used in place of the composition in Table 1 under Example 1.

Example 3

A dental prosthesis having porcelain coated on metal is made by mixing 3 parts of glass frit made as disclosed in Example 2 with one part of organic gel to form a paste. The gel is composed of glycerine, butylene glycol, diethylene glycol, preservative, cellulose, silica and water. The paste is then brushed onto metal base material to form a paste coating. 1 part of crystals made as disclosed in Table 1 under Example 3 are sprinkled onto the paste coating, for each 4 parts of paste coating, to form a paste with crystals embedded therein coating on the metal base. The crystal-embedded paste coating is then dried for 5 minutes, then preheated for 5 minutes at 450° C., then fired by heating to 785° C. at a heating rate of 90° C. per minute while under a vacuum of 29 inches of Hg between 450° C. and 765° C. and holding the temperature at 785 for 1 minute to form a light refractive surface opaque porcelain layer.

Example 4

3 parts of a glass frit having the composition in Table 1 under Example 4 are mixed with 1 part of water to form a thick paste. The paste is brushed onto the outer surface of the opaque porcelain layer of Example 3.

Example 4A and 4B

The procedure of Example 4 is followed except that the glass frit composition in Table 1A under Example 4A or 4B is used in place of that under Example 4 in Table 1.

Example 5

The procedure of Example 4 is followed except that the glass frit used is disclosed in Table 1 under Example 5.

DENTIN/ENAMEL LAYER

Example 5A

To the product of Example 3, an opaque porcelain layer, on a conventional dental ceramic palladium-gold-silver alloy, is applied 2 parts of the product of Example 4 and then a discrete, separate addition of 1 part of the product of Example 5 and then drying at 100° C. for 5 minutes, heating for 5 minutes at 450° C., followed by heating to 740° C. at a heating rate of 35° C. per minute while under a vacuum of 29 inches of Hg between 450° C. and 720° C. to form a dentin enamel layer on a crown.

Example 5B

The procedure of example 4 is followed except that the glass frit used is that disclosed in Table 1 under Example 5B.

Example 5C

The procedure of example 5A is followed, except that the glass frits of Examples 3 and 4 are replaced with the glass frits disclosed in Table 1 under Example 5B and Table 1A under Example 5C, respectively.

TABLE 1

| COMPONENTS | Example 1 LOW-FUSING POWDER OPAQUE (percent by weight) | Example 1A POWER OPAQUE MODIFIER (percent by weight) | Example 2 LOW-FUSING PASTE OPAQUE TRANSPARENT ENAMEL (percent by weight) | Example 2A PASTE OPAQUE MODIFIER (percent by weight) | Example 3 LOW-FUSING CRYSTALS (percent by weight) | Example 4 LOW-FUSING DENTIN (percent by weight) | Example 5 LOW-FUSING OPAL AND (percent by weight) | Example 5B LOW-FUSING DENTIN (percent by weight) |
|---|---|---|---|---|---|---|---|---|
| $SiO_2$ | 45.3 | 52.0 | 42.7 | 57.1 | 62.7 | 62.7 | 62.0 | 60.8 |
| $Al_2O_3$ | 7.1 | 7.8 | 6.6 | 8.2 | 11.2 | 8.4 | 8.9 | 8.6 |
| $K_2O$ | 10.1 | 11.4 | 9.5 | 9.7 | 8.4 | 5.9 | 6.1 | 12.2 |
| $Na_2O$ | 6.4 | 7.7 | 6.2 | 8.5 | 8.0 | 11.0 | 11.0 | 9.5 |
| $Li_2O$ | 1.6 | 1.7 | 1.5 | 1.5 | 2.0 | 2.4 | 2.4 | 1.7 |
| CaO | 1.1 | 2.4 | 1.1 | 1.9 | 1.6 | 1.0 | 2.0 | 1.9 |
| $CeO_2$ | 0.6 | 0.7 | 0.6 | 1.0 | 0.4 | 0.2 | 0.2 | 0.8 |
| MgO | --- | --- | --- | --- | 1.6 | 2.7 | 2.7 | 0.3 |
| $Tb_2O_3$ | --- | --- | --- | 0.4 | 1.0 | 1.2 | 1.2 | 1.4 |
| $B_2O_3$ | 1.1 | 1.3 | 1.1 | 1.3 | 2.0 | 3.5 | 3.5 | 1.4 |
| $Y_2O_3$ | 0.6 | 0.7 | 0.6 | 0.7 | 0.8 | --- | --- | --- |
| BaO | 1.1 | 1.3 | 1.1 | 1.7 | 0.3 | --- | --- | 1.4 |
| $TiO_2$ | --- | --- | 5.0 | --- | --- | --- | --- | --- |
| $ZrO_2$ | 18.0 | 7.0 | 15.0 | --- | --- | --- | --- | --- |
| $Y_2O_3$—$SiO_2$ | 7.0 | 7.0 | 9.0 | 8.0 | --- | --- | --- | <1 |
| Pigments | 10.0 | 35.0 | 10.0 | 15.0 | --- | <5 | <1 | <1 |

TABLE 1A

| COMPONENTS | Example 2A LOW-FUSING POWDER OPAQUE (percent by weight) | Example 4A LOW-FUSING DENTIN (percent by weight) | Example 4B LOW-FUSING DENTIN (percent by weight) | Example 5C LOW-FUSING OPAL ENAMEL (percent by weight) |
|---|---|---|---|---|
| $SiO_2$ | 45.2 | 59 | 59 | 58.4 |
| $Al_2O_3$ | 6.1 | 7 | 7 | 8.0 |
| $K_2O$ | 10.2 | 13.5 | 14.5 | 12.4 |
| $Na_2O$ | 7.3 | 10.5 | 10.5 | 9.3 |
| $Li_2O$ | 1.6 | 2 | 2 | 1.6 |
| CaO | 1.4 | 2 | 2 | 2.0 |
| $CeO_2$ | 0.7 | 1 | 1 | 1.1 |
| $Tb_2O_3$ | 0.7 | 1 | --- | 1.1 |
| $B_2O_3$ | 1.4 | 2 | --- | 1.5 |
| $Y_2O_3$ | --- | --- | 2 | --- |
| BaO | 1.4 | 2 | 2 | 1.8 |
| Pigments | (0–15) | <5 | <5 | <1 |
| $ZrO_2$ | 24.0 | <1 | <1 | <1 |
| $P_2O_5$ | --- | --- | 2.8 | --- |

TABLE 2

| Examples | LOW-FUSING POWDER OPAQUE 1 | LOW-FUSING PASTE OPAQUE 2 | LOW-FUSING CRYSTALS 3 | LOW-FUSING DENTIN 4 | LOW-FUSING OPAL AND TRANSPARENT ENAMEL 5 |
|---|---|---|---|---|---|
| Physical Property | | | | | |
| Flexural Strength (MPa) | 65 | 109 | — | 84 | 73 |
| Chemical Solubility* ($\mu g/cm^2$) | 183 | 92 | — | 42 | 77 |
| Glass Transition Temperature (GTT) (°C.) | | | | | |
| 2 firings | 460 | 500 | 486 | 465 | 464 |
| 4 firings | 464 | 500 | 484 | 462 | 461 |
| Thermal Expansion 25° C. — GTT | | | | | |
| 2 firings (ppm/K) | 11.9 | 12.2 | 12.3 | 12.1 | 12.4 |
| Thermal Stability | | | | | |
| 4 firings (ppm/K) | 12.4 | 12.2 | 11.9 | 12.0 | 12.3 |

*after 16 hours in boiling acetic acid.

TABLE 3

Firing Schedules for Porcelain

| Composition of Example number | Firing Program | Time (minutes) Dry | Pre-Heat | Vacuum Hold (inches in Hg) | Idle Temperature (°C.) | High Temperature (°C.) |
|---|---|---|---|---|---|---|
| 2, 3 | Paste Opaque and crystals | 5 | 5 | 0  29 | 450 | 785 |
| 1 | Powder opaque | 3 | 3 | 0  29 | 450 | 785 |
| 4 & 5 | Dentin and Enamel | 5 | 5 | 0  29 | 450 | 740 |
| 5B & 5C | Dentin and Enamel | 5 | 5 | 0  29 | 950 | 780 |

| Composition of Example number | Firing Program | Vacuum Start Temperature (°C.) | Vacuum Stop Temperature (°C.) | Heating Rate (°C./minutes) | High Temperature Hold (minutes) |
|---|---|---|---|---|---|
| 2, 3 | Paste Opaque and crystals | 450 | 765 | 70 | 1 |
| 1 | Powder opaque | 450 | 765 | 90 | 0 |
| 4 & 5 | Dentin and Enamel | 450 | 720 | 35 | 0 |
| 5B & 5C | Dentin and Enamel | 950 | 760 | 55 | 1 |

The compositions of Examples 1–5 are fired according to the schedules in Table 3. Thus, the composition of Example 2 and 3 are fired by first drying for 3 minutes, then preheating for 3 minutes to 450° C. and then heating from 450° C. to 785° C. under a vacuum of 29 inches of mercury at a rate of 70° C. per minute. At 765° C. the vacuum is released and heating is continued to 785° C.

Example 6

A powder opaque kit container is provided which supports and encloses eighteen bottles each containing 15 g of the product of Example 1 pigmented in sixteen Lumin™ of VITA Zahnfabrik shades, one AO shade and one BO shade; nine bottles of modifier porcelain each having 15 g of the composition of Example 1A and pigmented White, Gray, Pink, Violet, Ochre, Yellow, Tan, Orange or Sienna; a bottle containing 120 ml of carving Liquid, sold by Ceramco, Inc.; and two Finesse Opaque Shade Fans. Each bottle has a threaded body and a threaded cap. Each shade fan has eighteen porcelain chips. Each chip represents the shade of contents of one of the bottles containing one of the pigmented compositions of Examples 1 and 1A after firing as shown in Table 3.

Example 7

A paste opaque kit container is provided which supports and encloses eighteen syringes each having 2 ml of paste opaque porcelain, prepared as disclosed in Example 2 and pigmented in sixteen Lumin™ of VITA Zahnfabrik shades, one AO shade and one BO shade; nine bottles of modifier porcelain each having 3 ml of the composition of Example 2A, mixed with gel and pigmented White, Gray, Pink, Violet, Ochre, Yellow, Tan, Orange, or Sienna; a bowl; a bottle containing 10 g of crystals having the composition of Example 3; a brush for application of the pastes; a bottle containing 15 ml of Opaque Modifier Liquid, sold by Ceramco, Inc.; and two Opaque Shade Fans. Each shade fan has porcelain chips. Each chip represents one of the compositions of Example 2 and Example 2A in the eighteen syringes and nine bottles after being dispensed and then fired as shown in Table 3.

Example 8

A prosthesis is prepared by forming an alloy metal into a dental tooth crown shape and oxidizing or degassing alloy according to the alloy manufacturer's instructions. The powder opaque porcelain composition of Example 1 is then mixed with distilled water to a thin paste like consistency. The opaque paste is painted onto the alloy in a thin even layer, and condensed slightly to form an even coating on the outer surface of the alloy. The coated alloy is then fired according to Table 3. A second coat of powder opaque composition of Example 1 is then painted onto the alloy metal to completely mask it. Opaque modifiers are then applied. After condensing slightly to form an even coating outer surface the coated alloy is fired according to Table 3. The prosthesis product has a slight sheen after firing.

Example 8A

To 1 part of the product of Example 8 is applied, 2 parts of the product Example 4 having the composition shown in Table 1 and then 1 part of the product of Example 5 having the composition shown in Table 1. This coating is then fired accordingly to Table 3 under Example 4.

Example 9

A prosthesis is prepared by forming an alloy metal into a dental bridge shape, oxidizing or degassing the alloy according to the alloy manufacturer's instructions. Using a brush, the opaque paste composition of Example 2 is applied to the alloy in a thin even layer. The brush coated alloy is dried at 23° C. for 10 minutes and then fired according to Table 3. A second coat of the paste opaque porcelain paste composition of Example 2 is applied to the alloy metal to completely mask it. Opaque modifiers are then applied. Crystals are then sprinkled onto the second layer of the paste opaque and the coated alloy dental bridge restoration is fired according to Table 3. The restoration has a sandpaper or emery board appearance after firing.

Example 9A

To 1 part of the product of Example 9 is applied, 2 parts of the product Example 4 having the composition shown in Table 1 and then 1 part of the product of Example 5 having the composition shown in Table 1. This coating is then fired accordingly to Table 3 under Example 4.

A preferred embodiment of the invention provides a low-fusing temperature porcelain composition for use in a dental prosthesis, including, from 40 to 65 percent by weight $SiO_2$, from 6 to 12 percent by weight $Al_2O_3$, from 6 to 12 percent by weight $Na_2O$, from 5.5 to 10.5 percent by weight $K_2O$, from 1 to 3 percent by weight $Li_2O$, from 0.8 to 2.5 percent by weight CaO, from 0.5 to 4 percent by weight $B_2O_3$ and 0.1 to 0.8 percent by weight $CeO_2$ and from 0.01 to 3.0 percent by weight $P_2O_5$ and having a coefficient of thermal expansion of from about 11.5 to 12.5 ppm ° $K^{-1}$ [30° to 430° C.]. Preferably the low-fusing temperature porcelain composition further comprises from 0.5 to 1.5 percent by weight of $Tb_2O_3$, from 10 to 20 percent by weight $ZrO_2$ and from 5 to 10 percent by weight $Y_2O_3$—$SiO_2$.

A preferred embodiment of the invention provides a low-fusing temperature porcelain composition for use in a dental prosthesis, comprising, from 40 to 65 percent by weight $SiO_2$, from 6 to 12 percent by weight $Al_2O_3$, from 6 to 12 percent by weight $Na_2O$, from 5.5 to 10.5 percent by weight $K_2O$, from 1 to 3 percent by weight $Li_2O$, from 0.8 to 2.5 percent by weight CaO, from 0.5 to 4 percent by weight $B_2O_3$ and 0.1 to 0.8 percent by weight $CeO_2$ and at least 0.4 percent by weight of $Y_2O_3$.

A preferred embodiment of the invention provides a low-fusing temperature porcelain composition for use in a dental prosthesis, including a glass frit composition comprising from 40 to 65 percent by weight $SiO_2$, from 6 to 12 percent by weight $Al_2O_3$, from 6 to 12 percent by weight $Na_2O$, from 5.5 to 10.5 percent by weight $K_2O$, from 1 to 3 percent by weight $Li_2O$, from 0.8 to 2.5 percent by weight CaO, from 0.5 to 4 percent by weight $B_2O_3$, 0.1 to 0.8 percent by weight $CeO_2$, and from 0.5 to 3 percent by weight of MgO said glass frit composition having a processing temperature of about 705° C. and a coefficient of thermal expansion of from about 12 to 13 ppm ° $K^{-1}$ [20° to 500° C.].

A preferred embodiment of the invention provides a low-fusing temperature porcelain composition for use in a dental prosthesis, comprising a glass frit composition comprising from 40 to 65 percent by weight $SiO_2$, from 6 to 12 percent by weight $Al_2O_3$, from 6 to 12 percent by weight $Na_2O$, from 5.5 to 10.5 percent by weight $K_2O$, from 1 to 3 percent by weight $Li_2O$, from 0.8 to 2.5 percent by weight CaO, from 0.5 to 4 percent by weight $B_2O_3$ and 0.1 to 0.8 percent by weight $CeO_2$, said glass frit composition having a processing temperature of about 705° C. and a coefficient of thermal expansion of from about 12 to 13 ppm ° $K^{-1}$ [20° to 500° C.] and from 40 to 47 percent by weight $SiO_2$, from 6 to 8 percent by weight $Al_2O_3$, from 8 to 12 percent by weight $Na_2O$, from 9.0 to 10.5 percent by weight $K_2O$, from 1 to 2 percent by weight $Li_2O$, from 0.8 to 1.5 percent by weight CaO, from 0.8 to 1.5 percent by weight $B_2O_3$ and from 0.3 to 0.8 percent by weight $CeO_2$. Preferably the low-fusing temperature porcelain composition further comprises from 0.5 to 1.5 percent by weight of $Tb_2O_3$, from 10 to 20 percent by weight $ZrO_2$ and from 5 to 10 percent by weight $Y_2O_3$—$SiO_2$.

A preferred embodiment of the invention provides a low-fusing temperature porcelain composition for use in a dental prosthesis, comprising a glass frit composition comprising from 40 to 65 percent by weight $SiO_2$, from 6 to 12 percent by weight $Al_2O_3$, from 6 to 12 percent by weight $Na_2O$, from 5.5 to 10.5 percent by weight $K_2O$, from 1 to 3 percent by weight $Li_2O$, from 0.8 to 2.5 percent by weight CaO, from 0.5 to 4 percent by weight $B_2O_3$ 0.1 to 0.8 percent by weight $CeO_2$, and from 0.5 to 3 percent by weight of MgO said glass frit composition having a processing temperature of about 705° C. and a coefficient of thermal expansion of from about 12 to 13 ppm ° $K^{-1}$ [20° to 500° C.].

A preferred embodiment of the invention provides a low-fusing temperature porcelain composition for use in a dental prosthesis, comprising a glass frit composition comprising from 40 to 47 percent by weight $SiO_2$, from 6 to 8 percent by weight $Al_2O_3$, from 8 to 12 percent by weight $Na_2O$, from 9.0 to 10.5 percent by weight $K_2O$, from 1 to 2 percent by weight $Li_2O$, from 0.8 to 1.5 percent by weight CaO, from 0.8 to 1.5 percent by weight $B_2O_3$ and from 0.3 to 0.8 percent by weight $CeO_2$, said glass frit composition having a processing temperature of about 705° C. and a coefficient of thermal expansion of from about 12 to 13 ppm ° $K^{-1}$ [20° to 500° C.]. Preferably the low-fusing temperature porcelain composition further comprises from 0.5 to 1.5 percent by weight of $Tb_2O_3$, from 10 to 20 percent by weight $ZrO_2$ and from 5 to 10 percent by weight $Y_2O_3$—$SiO_2$.

A preferred embodiment of the invention provides a method of making a dental prosthesis, comprising providing and shaping a low-fusing temperature porcelain composition for use in a dental prosthesis, comprising, from 40 to 47 percent by weight $SiO_2$, from 6 to 8 percent by weight $Al_2O_3$, from 8 to 12 percent by weight $Na_2O$, from 9.0 to 10.5 percent by weight $K_2O$, from 1 to 2 percent by weight Li$_2$O, from 0.8 to 1.5 percent by weight CaO, from 0.8 to 1.5 percent by weight B$_2$O$_3$ and from 0.3 to 0.8 percent by weight CeO$_2$ and heating said composition to between 740° C. and 800° C. to make a dental prosthesis.

A preferred embodiment of the invention provides a kit comprising a container support and at least three containers supported by said container support, each of said containers enclosing a low-fusing temperature porcelain composition for use in a dental prosthesis, comprising, from 40 to 47 percent by weight SiO$_2$, from 6 to 8 percent by weight Al$_2$O$_3$, from 8 to 12 percent by weight Na$_2$O, from 9.0 to 10.5 percent by weight K$_2$O, from 1 to 2 percent by weight Li$_2$O, from 0.8 to 1.5 percent by weight CaO, from 0.8 to 1.5 percent by weight B$_2$O$_3$ and from 0.3 to 0.8 percent by weight CeO$_2$.

Another preferred embodiment of the invention provides a low-fusing composition for use in a dental prosthesis, comprising form 40 to 65 percent by weight SiO$_2$, from 6 to 12 percent by weight Al$_2$O$_3$, from 6 to 12 percent by weight Na$_2$O, from 5.5 to 10.5 percent by weight K$_2$O, from 1 to 3 percent by weight Li$_2$O, from 0.8 to 2.5 percent by weight CaO, from 0.5 to 4 percent by weight B$_2$O$_3$, 0.1 to 0.8 percent by weight CeO$_2$, from 0.5 to 2 percent by weight Tb$_2$O$_3$ and from 1 to 3 percent by weight MgO.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A low-fusing temperature porcelain composition for use in a dental prosthesis, comprising, from 40 to 65 percent by weight SiO$_2$, from 6 to 12 percent by weight Al$_2$O$_3$, from 6 to 12 percent by weight Na$_2$O, from 5.5 to 10.5 percent by weight K$_2$O, from 1 to 3 percent by weight Li$_2$O, from 0.8 to 2.5 percent by weight CaO, from 0.5 to 4 percent by weight B$_2$O$_3$ and 0.1 to 0.8 percent by weight CeO$_2$ and from 0.01 to 3.0 percent by weight P$_2$O$_5$ and having a coefficient of thermal expansion of from about 11.5 to 12.5 ppm ° K$^{-1}$ [30° to 430° C.].

2. The porcelain of claim 1, having a fusing temperature of less than 800° C. and a coefficient of thermal expansion compatible with a substrate of metal or ceramic suitable for a dental prosthetic.

3. A low-fusing temperature porcelain composition for use in a dental prosthesis, comprising, from 40 to 65 percent by weight SiO$_2$, from 6 to 12 percent by weight Al$_2$O$_3$, from 6 to 12 percent by weight Na$_2$O, from 5.5 to 10.5 percent by weight K$_2$O, from 1 to 3 percent by weight Li$_2$O, from 0.8 to 2.5 percent by weight CaO, from 0.5 to 4 percent by weight B$_2$O$_3$ and 0.1 to 0.8 percent by weight CeO$_2$ and from 0.5 to 2 percent by weight of Tb$_2$O$_3$ and from 1 to 3 percent by weight MgO.

4. A low-fusing temperature porcelain composition for use in a dental prosthesis, comprising, from 40 to 65 percent by weight SiO$_2$, from 6 to 12 percent by weight Al$_2$O$_3$, from 6 to 12 percent by weight Na$_2$O, from 5.5 to 10.5 percent by weight K$_2$O, from 1 to 3 percent by weight Li$_2$O, from 0.8 to 2.5 percent by weight CaO, from 0.5 to 4 percent by weight B$_2$O$_3$ and 0.1 to 0.8 percent by weight CeO$_2$ and at least 0.4 percent by weight of Y$_2$O$_3$.

5. A low-fusing temperature porcelain composition for use in a dental prosthesis, comprising, from 58 to 65 percent by weight SiO$_2$, from 6 to 12 percent by weight Al$_2$O$_3$, from 7 to 12 percent by weight Na$_2$O, from 5.5 to 18.0 percent by weight K$_2$O, from 1.5 to 3 percent by weight Li$_2$O, from 1.2 to 2.5 percent by weight CaO, from 0.5 to 4 percent by weight and from 0.1 to 2.0 percent by weight CeO$_2$.

6. A low-fusing temperature porcelain composition for use in a dental prosthesis, comprising, from 40 to 47 percent by weight SiO$_2$, from 5 to 8 percent by weight Al$_2$O$_3$, from 6 to 12 percent by weight Na$_2$O, from 9.0 to 10.5 percent by weight K$_2$O, from 1 to 3 percent by weight Li$_2$O, from 0.8 to 3.0 percent by weight CaO, from 0.8 to 2.0 percent by weight B$_2$O$_3$ and from 0.3 to 1.0 percent by weight CeO$_2$.

7. The porcelain of claim 1, wherein said composition comprises from 60 to 65 percent by weight SiO$_2$, from 8 to 12 percent by weight Al$_2$O$_3$, from 7 to 12 percent by weight Na$_2$O, from 5.5 to 9.0 percent by weight K$_2$O, from 1.5 to 3 percent by weight Li$_2$O, from 1.2 to 2.5 percent by weight CaO, from 1.5 to 4.0 percent by weight B$_2$O$_3$ and from 0.1 to 0.6 percent by weight CeO$_2$.

8. A low-fusing temperature porcelain composition for use in a dental prosthesis comprising, from 40 to 47 percent by weight SiO$_2$, from 6 to 8 percent by weight Al$_2$O$_3$, from 8 to 12 percent by weight Na$_2$O, from 9.0 to 10.5 percent by weight K$_2$O, from 1 to 2 percent by weight Li$_2$O, from 0.8 to 1.5 percent by weight CaO, from 0.8 to 1.5 percent by weight B$_2$O$_3$ and from 0.3 to 0.8 percent by weight CeO$_2$.

9. The porcelain of claim 7 further comprising from 0.5 to 3 percent by weight of MgO.

10. The porcelain of claim 5 further comprising from 0.5 to 1.5 percent by weight of Tb$_2$O$_3$.

11. The porcelain of claim 5 further comprising from 10 to 20 percent by weight ZrO$_2$.

12. The porcelain of claim 7 further comprising from 5 to 10 percent by weight Y$_2$O$_3$—SiO$_2$.

13. A low-fusing temperature porcelain composition for use in a dental prosthesis, comprising a glass frit composition comprising from 40 to 65 percent by weight SiO$_2$, from 6 to 12 percent by weight Al$_2$O$_3$, from 6 to 12 percent by weight Na$_2$O, from 5.5 to 10.5 percent by weight K$_2$O, from 1 to 3 percent by weight Li$_2$O, from 0.8 to 2.5 percent by weight CaO, from 0.5 to 4 percent by weight B$_2$O$_3$, 0.1 to 0.8 percent by weight CeO$_2$, and from 0.5 to 3 percent by weight of MgO said glass frit composition having a processing temperature of about 705° C. and a coefficient of thermal expansion of from about 12 to 13 ppm ° K$^{-1}$ [20° to 500° C.].

14. The low-fusing temperature porcelain composition for use in a dental prosthesis of claim 13, wherein said composition comprises from 60 to 65 percent by weight SiO$_2$, from 8 to 12 percent by weight Al$_2$O$_3$, from 7 to 12 percent by weight Na$_2$O, from 5.5 to 9.0 percent by weight K$_2$O, from 1.5 to 3 percent by weight Li$_2$O, from 1.2 to 2.5 percent by weight CaO, from 1.5 to 4.0 percent by weight B$_2$O$_3$ and from 0.1 to 0.6 percent by weight CeO$_2$.

15. A low-fusing temperature porcelain composition for use in a dental prosthesis, comprising a glass frit composition comprising from 40 to 47 percent by weight SiO$_2$, from 6 to 8 percent by weight Al$_2$O$_3$, from 8 to 12 percent by weight Na$_2$O, from 9.0 to 10.5 percent by weight K$_2$O, from 1 to 2 percent by weight Li$_2$O, from 0.8 to 1.5 percent by weight CaO, from 0.8 to 1.5 percent by weight B$_2$O$_3$ and from 0.3 to 0.8 percent by weight CeO$_2$, said glass frit composition having a processing temperature of about 705° C. and a coefficient of thermal expansion of from about 12 to 13 ppm ° K$^{-1}$ [20° to 500° C.].

16. The low-fusing temperature porcelain composition for use in a dental prosthesis of claim 14 further comprising from 0.5 to 1.5 percent by weight of Tb$_2$O$_3$.

17. The low-fusing temperature porcelain composition for use in a dental prosthesis of claim 15 further comprising from 10 to 20 percent by weight ZrO$_2$.

18. The low-fusing temperature porcelain composition for use in a dental prosthesis of claim 15 further comprising from 5 to 10 percent by weight $Y_2O_3$—$SiO_2$.

19. A method of making a dental prosthesis, comprising:
providing and shaping a low-fusing temperature porcelain composition for use in a dental prosthesis, comprising, from 40 to 47 percent by weight $SiO_2$, from 6 to 8 percent by weight $Al_2O_3$, from 8 to 12 percent by weight $Na_2O$, from 9.0 to 10.5 percent by weight $K_2O$, from 1 to 2 percent by weight $Li_2O$, from 0.8 to 1.5 percent by weight CaO, from 0.8 to 1.5 percent by weight $B_2O_3$ and from 0.3 to 0.8 percent by weight $CeO_2$ and heating said composition to between 740° C. and 800° C. to make a dental prosthesis.

20. The method according to claim 19, wherein the glass frit is fused to a ceramic substrate to form the dental prosthesis.

21. The method according to claim 19, wherein the glass frit is fused to a ceramic or metal substrate to form the dental prosthesis.

22. The method of claim 19 wherein said composition comprises from 60 to 65 percent by weight $SiO_2$, from 8 to 12 percent by weight $Al_2O_3$, from 7 to 12 percent by weight $Na_2O$, from 5.5 to 9.0 percent by weight $K_2O$, from 1.5 to 3 percent by weight $Li_2O$, from 1.2 to 2.5 percent by weight CaO, from 1.5 to 4.0 percent by weight $B_2O_3$ and from 0.1 to 0.6 percent by weight $CeO_2$.

23. A kit comprising a container support and at least three containers supported by said container support, each of said containers enclosing a low-fusing temperature porcelain composition for use in a dental prosthesis, comprising, from 40 to 47 percent by weight $SiO_2$, from 6 to 8 percent by weight $Al_2O_3$, from 8 to 12 percent by weight $Na_2O$, from 9.0 to 10.5 percent by weight $K_2O$, from 1 to 2 percent by weight LiO, from 8 to 12 percent by weight CaO, from 0.8 to 1.5 percent by weight $B_2O_3$ and from 0.3 to 0.8 percent by weight $CeO_2$.

24. The kit of claim 23 wherein said composition comprises from 60 to 65 percent by weight $SiO_2$, from 8 to 12 percent by weight $Al_2O_3$, from 7 to 12 percent by weight $Na_2O$, from 5.5 to 9.0 percent by weight $K_2O$, from 1.5 to 3 percent by weight $Li_2O$, from 1.2 to 2.5 percent by weight CaO, from 1.5 to 4.0 percent by weight $B_2O_3$ and from 0.1 to 0.6 percent by weight $CeO_2$.

25. The kit of claim 23 wherein each of said containers is a syringe.

26. The kit of claim 23 wherein each of said containers comprises a threaded cap and a threaded base.

* * * * *